United States Patent [19]

Erickson et al.

[11] Patent Number: 5,176,137
[45] Date of Patent: Jan. 5, 1993

[54] APPARATUS FOR DISCRIMINATION OF STABLE AND UNSTABLE VENTRICULAR TACHYCARDIA AND FOR TREATMENT THEREOF

[75] Inventors: Mark K. Erickson, Minneapolis; Tom D. Bennett, Shoreview, both of Minn.

[73] Assignee: Medtronic, Inc., Minneapolis, Minn.

[21] Appl. No.: 663,985

[22] Filed: Mar. 1, 1991

[51] Int. Cl.⁵ .............................................. A61N 1/39
[52] U.S. Cl. .............................................. 128/419 D
[58] Field of Search ..................... 128/419 D, 419 PG

[56] References Cited

U.S. PATENT DOCUMENTS

| Re. 27,757 | 3/1987 | Mirowski . |
|---|---|---|
| 3,737,579 | 6/1973 | Bolduc . |
| 4,114,628 | 9/1978 | Rizk . |
| 4,240,442 | 12/1980 | Andresen et al. . |
| 4,291,699 | 9/1981 | Geddes et al. . |
| 4,375,817 | 3/1983 | Engle et al. . |
| 4,384,585 | 5/1983 | Zipes . |
| 4,523,595 | 6/1985 | Zibell . |
| 4,548,209 | 10/1985 | Wielders et al. . |
| 4,577,633 | 3/1986 | Berkovits et al. . |
| 4,587,970 | 5/1986 | Holley et al. . |
| 4,693,253 | 9/1987 | Adams . |
| 4,726,380 | 2/1988 | Vollmann et al. . |
| 4,750,495 | 6/1988 | Moore et al. . |
| 4,774,950 | 10/1988 | Cohen . |
| 4,800,883 | 1/1989 | Winstrom . |
| 4,817,634 | 4/1989 | Holleman et al. . |
| 4,819,643 | 4/1989 | Menken . |
| 4,830,006 | 5/1989 | Haluska et al. . |
| 4,880,004 | 11/1989 | Baker, Jr. et al. . |
| 4,880,005 | 11/1989 | Pless et al. . |
| 4,949,719 | 8/1990 | Pless et al. . |
| 4,953,551 | 9/1990 | Mehra et al. . |
| 4,967,748 | 11/1990 | Cohen . |
| 4,967,749 | 11/1990 | Cohen . |

OTHER PUBLICATIONS

"Experimental Ventricular Defibrillation with an Automatic and Completely Implanted System", Transactions American Society for Artificial Internal Organs, 16:207 1970, by Schuder et al.
"Automatic Implantable Cardioverter-Defibrillator Structural Characteristics", PACE, vol. 7, Nov.-Dec. 1984, Part II, pp. 1331-1334, by Mower et al.
"Reliable R-Wave Detection from Ambulatory Subjects", by Thakor, Biomed Sci Instrum 14:67-72, 1978.
"Relationship Between Right Atrial and Mixed Venous Oxygen Saturation and Heart Rate During Exercise in Normal Subjects and Patients with Cardiac Disease" by a French et al.

*Primary Examiner*—William E. Kamm
*Attorney, Agent, or Firm*—Reed A. Duthler; Harold R. Patton

[57] ABSTRACT

A method and apparatus for discriminating between stable and unstable ventricular tachycardias based on a measurement of oxygen saturation. Reference values for average oxygen saturation level and of the pulsatile characteristic of the oxygen saturation level are taken while a patient is in a resting condition. Measurements of oxygen saturation are also taken in response to the detection of a high heart rate, and are compared to the reference measurements to discriminate between stable and unstable ventricular tachyarrhythmias. An unstable tachyarrhythmia is diagnosed if a tachycardia is diagnosed and the current oxygen saturation level is similar to the reference average oxygen saturation level or if the oxygen saturation as presently measured displays a decreased pulsatile characteristic as compared to the reference measurements. The discriminator is intended for use in conjunction with or as part of an automated cardioverter of the type capable of delivering differing therapies for termination of stable and unstable ventricular tachyarrhythmias, such as antitachycardia pacing, cardioversion and defibrillation.

20 Claims, 7 Drawing Sheets

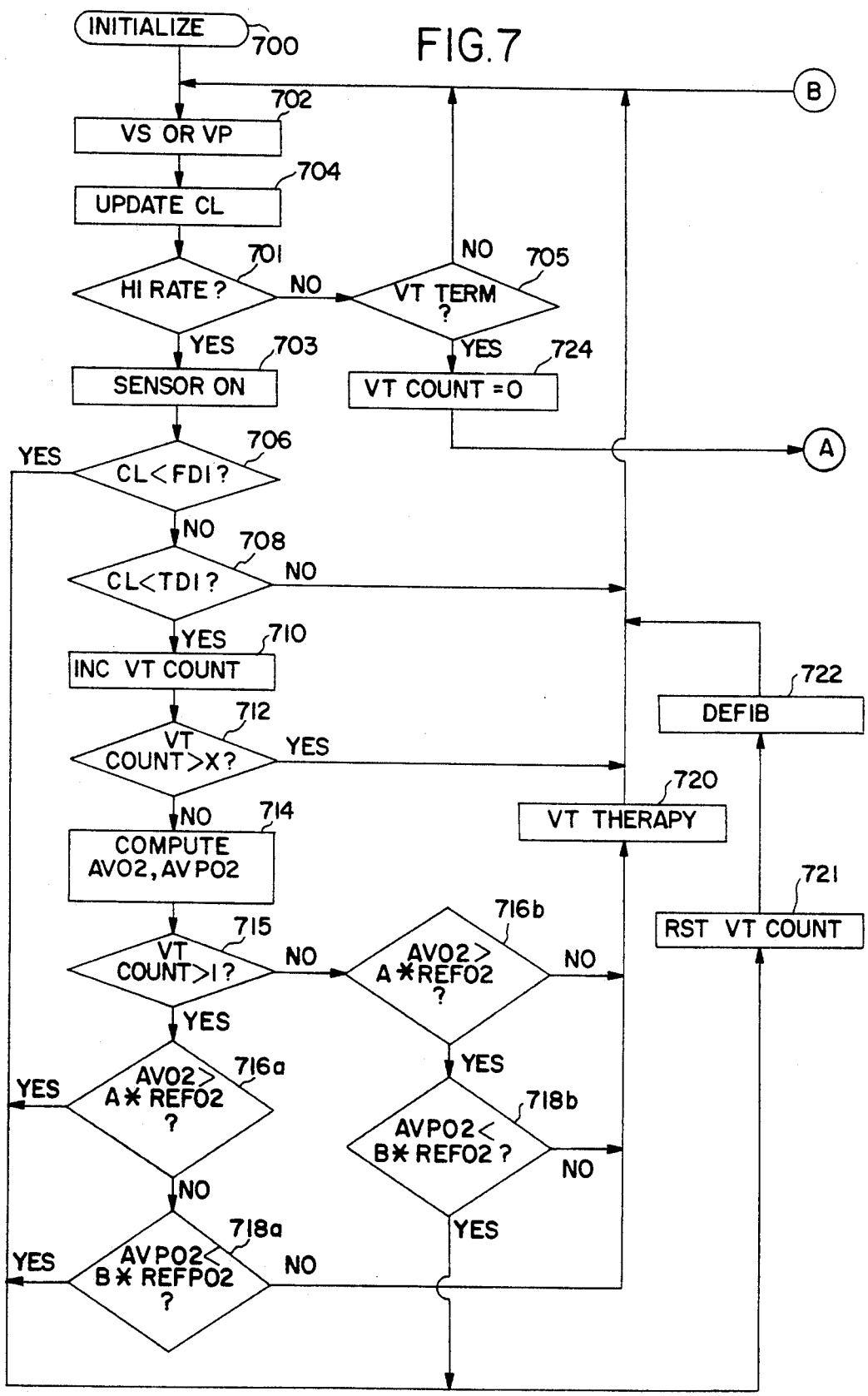

APPARATUS FOR DISCRIMINATION OF STABLE AND UNSTABLE VENTRICULAR TACHYCARDIA AND FOR TREATMENT THEREOF

BACKGROUND OF THE INVENTION

This invention relates to implantable stimulators generally and more particularly to implantable cardioverters and defibrillators.

Early automatic tachycardia detection systems for automatic implantable cardioverter/defibrillators relied upon the presence or absence of electrical and mechanical heart activity (such as intramyocardial pressure, blood pressure, impedance, stroke volume or heart movement) and or the rate of the electrocardiogram to detect hemodynamically compromising ventricular tachycardia or fibrillation.

For example, the 1961 publication by Dr. Fred Zacouto, Paris, France, entitled, "Traitement D'Urgence des Differents Types de Syncopes Cardiaques du Syndrome de Morgangni-Adams-Stokes" (National Library of Medicine, Bethesda, MD) describes an automatic pacemaker and defibrillator responsive to the presence or absence of the patient's blood pressure in conjunction with the rate of the patient's electrocardiogram to diagnose and automatically treat brady and tachyarrhythmias. Later detection algorithms proposed by Satinsky, "Heart Monitor Automatically Activates Defibrillator", Medical Tribune, 9, No. 91:3, Nov. 11, 1968, and Shuder et al "Experimental Ventricular Defibrillation with an Automatic and Completely Implanted System", Transactions American Society for Artificial Internal Organs, 16:207, 1970, automatically detected and triggered defibrillation when the amplitude of the R-wave of the electrocardiogram fell below a predetermined threshold over a predetermined period of time.

The initial system proposed by Mirowski et al in U.S. Pat. No. Re 27,757, which relied upon the decrease in the amplitude of a pulsatile right ventricular pressure signal below a threshold over a predetermined period of time, was abandoned by Mirowski et al in favor of the rate and/or probability density function morphology discrimination as described in Mower et al, "Automatic Implantable Cardioverter-Defibrillator Structural Characteristics", PACE, Vol. 7, November–December 1984, Part II, pp. 1331–1334.

Sensing of the mechanical pumping action of the heart in conjunction with loss of ability to pace the heart as a method of fibrillation detection is taught in U.S. Pat. No. 4,144,628, issued to Rizk. Monitoring the intracardiac impedance to detect pumping action in conjunction with ECG analysis is taught as a method of fibrillation detection in U.S. Pat. No. 4,291,699, issued to Geddes et al.

More recently, others have suggested the use of high rate plus acceleration of rate or "onset" (U.S. Pat. No. 4,384,585) with sustained high rate and rate stability (U.S. Pat. No. 4,523,595) to distinguish among tachyarrhythmias. As stated in the article "Automatic Tachycardia Recognition", by R. Arzbaecher et al, PACE, May–June 1984, pp. 541–547, anti-tachycardia pacemakers that were undergoing clinical studies prior to the publication of that article detected tachycardia by sensing a high rate in the chamber to be paced. The specific criteria to be met before attempting tachyarrhythmia termination by pacing involved a comparison of the detected heart rate to a preset threshold, such as 150 beats per minute (400 millisecond cycle length) for a preselected number of beats. As stated above, other researchers had suggested the rate of change of rate or suddenness of onset, rate stability and sustained high rate as additional criteria to distinguish among various types of tachyarrhythmias.

Very generally, the systems that depend upon the aforementioned rate criteria are capable of discriminating tachycardia in greater or lesser degree from normal heart activity but can have difficulty in discriminating ventricular tachycardias from supraventricular tachycardias in some cases or in discriminating stable tachycardias from unstable tachyarrhythmias in which cardiac function is compromised. These difficulties may result in delivery of inappropriate antitachycardia pacing, cardioversion or defibrillation therapies.

Very recently, the concept of employing a physiologic sensor in conjunction with ECG analysis as a method of tachyarrhythmia detection and identification has been revived. Use of pressure sensors is addressed in U.S. Pat. Nos. 4,744,950 and 4,967,749, both issued to Cohen. The use of an oxygen saturation sensor is addressed in U.S. Pat. No. 4,967,748, also issued to Cohen.

SUMMARY OF THE INVENTION

In the context of an automatic implantable device for treating bradyarrhythmias, tachyarrhythmias and fibrillation, the present invention comprises a method and apparatus for reliable discrimination of stable ventricular tachycardias from unstable ventricular tachycardias and fibrillation. The discriminator of the present invention employs an oxygen saturation sensor.

The inventors of the present application have determined that an oxygen saturation sensor may be beneficially employed in two fashions to distinguish stable ventricular tachycardia during which the heart is not hemodynamically compromised from unstable ventricular tachycardia and fibrillation, in which hemodynamic functioning is either absent or severely reduced. The inventors of the present application have determined by continuous oxygen saturation measurements that the oxygen saturation of venous return blood as measured within the right ventricle of the heart displays a pulsatile characteristic when normal hemodynamic functioning is present. In the absence of normal hemodynamic functioning, the oxygen saturation level ceases to display this pulsatile characteristic, and this change can be used to diagnose the presence of an unstable ventricular tachycardia or fibrillation, and for triggering delivery of a defibrillation pulse. In addition, the inventors have determined that while the measured oxygen saturation level in venous return blood within the right ventricle of the heart drops substantially in the presence of a sinus tachycardia or other stable ventricular tachycardia in which hemodynamic functioning persists, the presence of a stable, invariant oxygen saturation level is to be expected during periods of hemodynamic compromise. This characteristic too can be used alone, or in conjunction with EKG analysis to detect the presence of a tachyarrhythmia requiring delivery of a defibrillation pulse. Conversely, in the absence of either of these two characteristics, delivery of antitachycardia pacing or cardioversion pulses may be indicated.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which:

FIGS. 5, 6 and 7 are functional flow charts illustrating methods of discrimination between unstable and stable ventricular tachycardia provided by the present invention, and illustrating the operation of the discriminator of the present invention as embodied in a microprocessor based device.

DETAILED DESCRIPTION OF THE PREFERRED EMBODIMENTS

Figure 1:
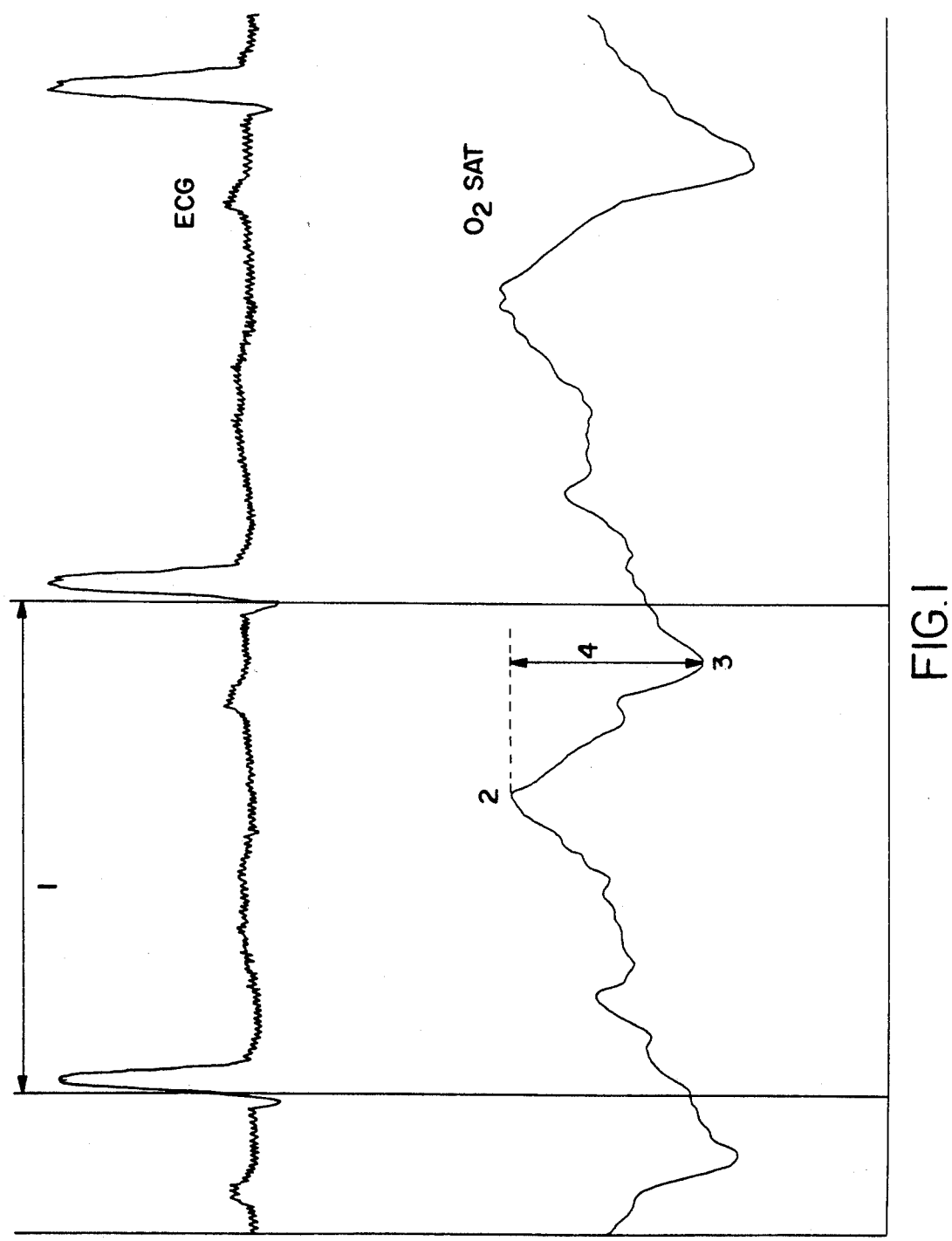
FIG. 1 is an ECG tracing, illustrating the theory underlying the present invention.

FIG. 1 is a simulated ECG strip and associated oxygen saturation tracing illustrating the theory underlying the present invention. The ECG tracing illustrates two R waves, and the interval therebetween, labeled "1" can be measured to determine the cycle length of the cardiac rhythm. This corresponds to the primary mechanism for monitoring heart rate used in prior art implantable cardioverters and defibrillators. The oxygen saturation tracing, labeled $O_2SAT$ illustrates the analog output of a two wavelength, reflectance oximeter as disclosed in U.S. Pat. No. 4,750,495, issued to Moore et al located within the right ventricle of the heart, and operating continuously to measure oxygen saturation. As can be seen in this figure, during normal heart functioning, the oxygen saturation signal is pulsatile, having a minimum saturation percentage 2 and a maximum saturation percentage 3 during each cardiac cycle. The difference 4 between the minimum and maximum saturation percentages may be measured and used in conjunction with the present invention to detect compromise of the hemodynamic pumping efficiency of the heart, in conjunction with high rate tachycardia and tachyarrhythmias. For purposes of the present application, this measured difference 4 is referred to as the oxygen saturation pulse amplitude. In the presence of hemodynamic compromise, the pulsatile characteristic of the $O_2SAT$ level is diminished or disappears altogether, as flow of blood through the heart ceases.

In the present invention, the $O_2SAT$ signal may be monitored and averaged over various time intervals. Measurements of the average $O_2SAT$ level are taken during normal heart rhythm at a rate great enough to inhibit the cardiac pacemaking function of the implanted pacemaker/cardioverter/defibrillator, but at a rate less than that which would indicate either a tachycardia or strenuous physical exercise. This base, resting measurement of oxygen saturation may be used to define an average oxygen saturation reference value (REFO2) and an average oxygen saturation pulse amplitude (REFPO2). REFO2 may be compared against the current average level of oxygen saturation (AVO2). If the presently measured level of oxygen saturation is not significantly less than this reference level, and the sensed cycle length is such that presence of a tachycardia is indicated, the device of the present invention may determine that the tachycardia is unstable, and trigger delivery of a defibrillation pulse.

Alternatively or additionally, REFPO2 may be compared against the current average oxygen saturation pulse amplitude (AVPO2). If the presently measured oxygen saturation pulse amplitude is significantly less than this reference level, and the sensed cycle length is such that presence of a tachycardia is indicated, the device of the present invention may determine that the tachycardia is unstable, and trigger delivery of a defibrillation pulse. Conversely, if the current oxygen saturation amplitude is significantly less than the reference level and/or the current oxygen saturation pulse amplitude is not significantly less than the reference pulse amplitude, the device determines that the detected tachycardia is stable and triggers delivery of an antitachycardia pacing therapy or a cardioversion pulse.

Figure 2:
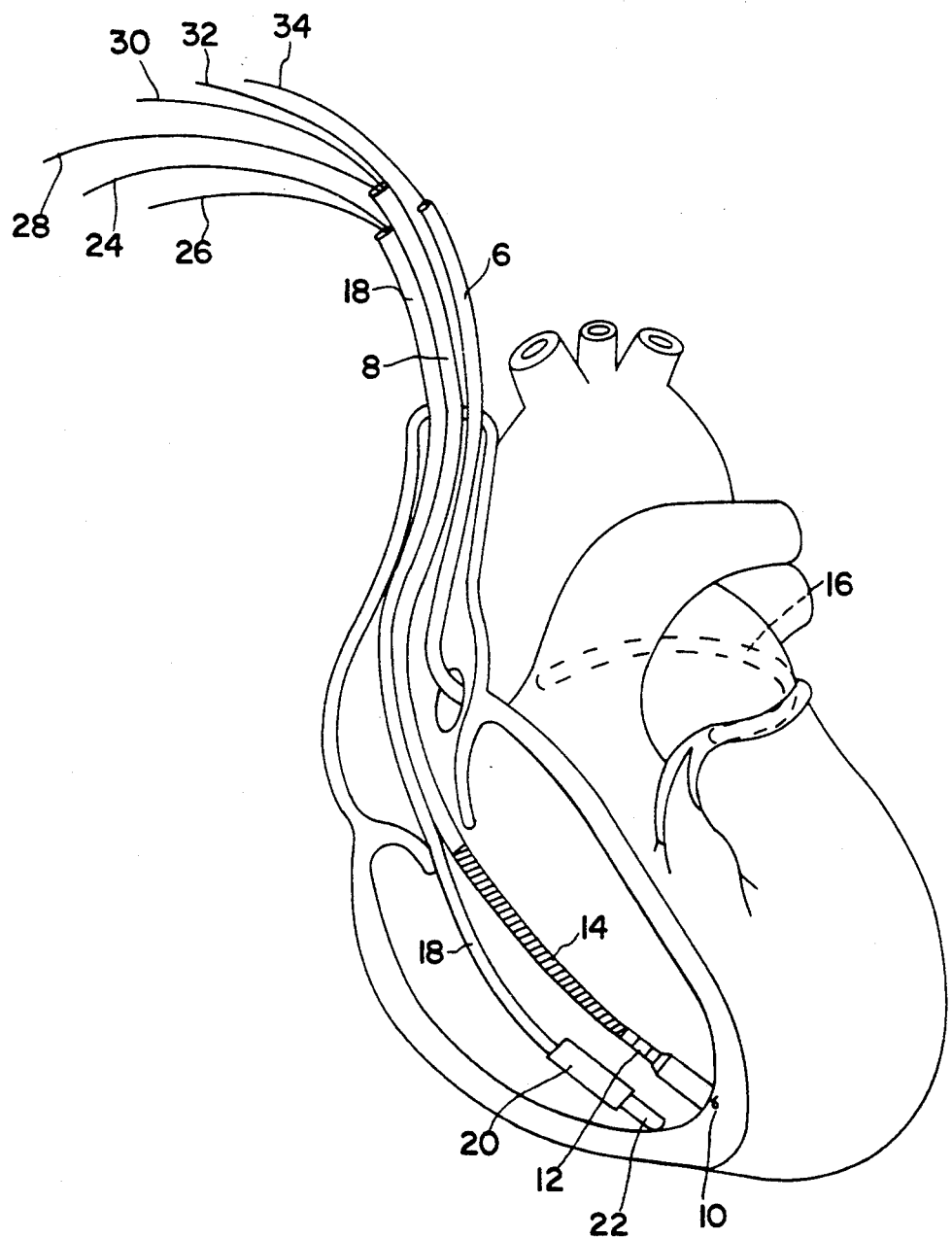
FIG. 2 illustrates one embodiment of a lead system for cardiac pacing, cardioversion and defibrillation which may be used in conjunction with the present invention.

FIG. 2 is a cutaway view of the heart and a plan view of an implantable pacing, cardioversion and defibrillation lead system. A ventricular defibrillation lead 8 carrying a bipolar electrode pair located at the right ventricular apex. The electrode pair includes a tip electrode 10, which takes the form of a helical electrode screwed into the right ventricular myocardium and a ring electrode 12. The lead also includes an elongated coiled defibrillation electrode 14. The illustrated lead corresponds generally to the ventricular lead described in U.S. Pat. No. 5,014,696 by Mehra for an Endocardial Defibrillation Electrode System, incorporated herein by reference in its entirety, but other defibrillation leads may also be employed.

The lead system also comprises a coronary sinus lead 6 and may optionally include a subcutaneous lead, not illustrated. The coronary sinus lead 6 is provided with an elongated electrode located in the coronary sinus and great vein in the region illustrated by broken outline at 16, extending around the heart until approximately the point at which the great vein turns downward, toward the apex of the heart. Lead 6 may also correspond to the coronary sinus lead disclosed in U.S. Pat. No. 5,014,696 by Mehra, cited above. If a subcutaneous electrode is also used, it generally will be implanted in the left chest and may correspond to the electrode illustrated in U.S. Pat. No. 5,044,374, by Lindemans et al. for a Medical Electrical Lead, filed July 7, 1989 and incorporated herein by reference in its entirety.

Also included is an oxygen saturation sensing lead 18, which carries a two wavelength reflectance oximeter 20, mounted adjacent a pliant distal end member 22. For purposes of the present invention, the sensor is preferably located in the right ventricle. The oxygen sensor may correspond to the sensor disclosed in U.S. Pat. No. 4,750,495, issued June 14, 1988 to Moore et al, incorporated herein by reference in its entirety. This lead is provided with two mutually insulated conductors, illustrated schematically at 24, 26. The sensor 20 includes an oscillator which sequentially activates red and infrared diodes. The duty cycle of the oscillator is regulated by the relative amounts of red and infrared light reflected by the blood. The duty cycle of the oscillator is reflected by modulation of the current drawn by the oscillator over conductors 24, 26, and thus provides a signal which can be demodulated to provide a measurement of oxygen saturation. While sensor 20 is shown mounted on a separate lead, it may also be incorporated on a lead such as lead 8, mounted distal to defibrillation electrode 14. Alternatively, sensor lead 18 may be provided with an electrode or electrodes at its distal end which may be used for pacing and sensing in the ventricle.

Figure 3:
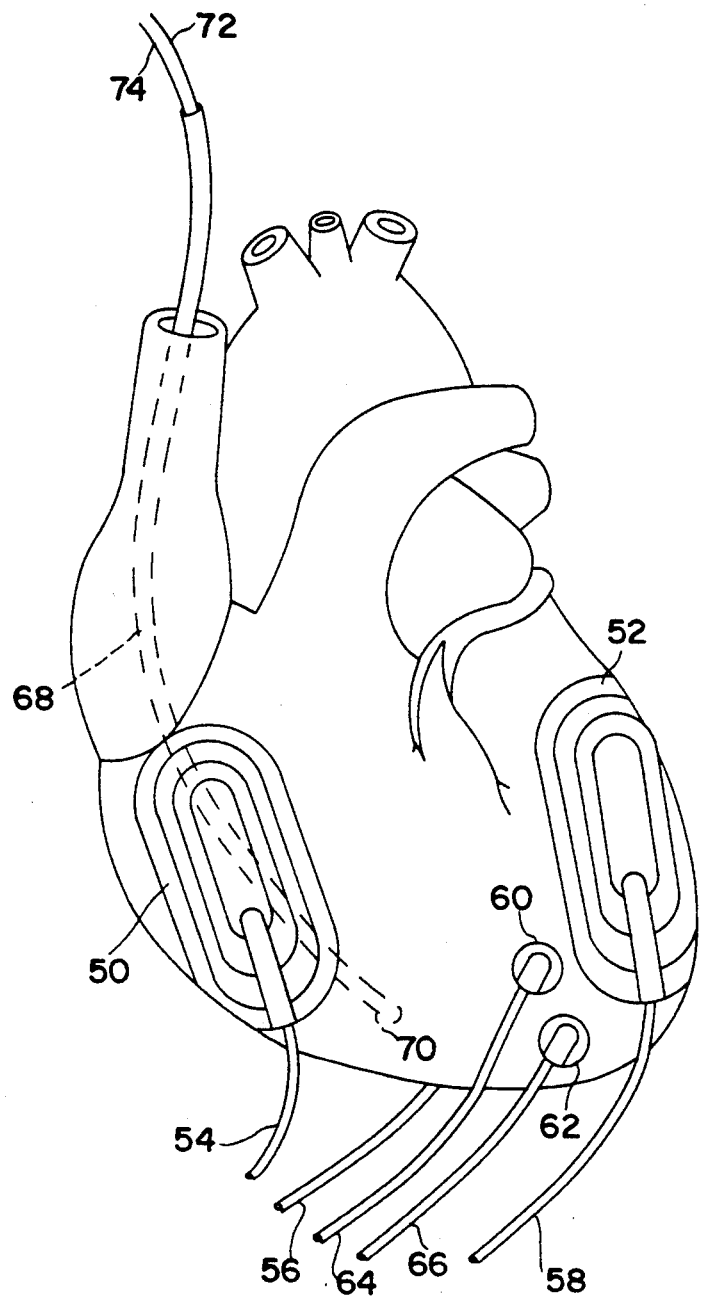
FIG. 3 illustrates another embodiment of a lead system for cardiac pacing, cardioversion and defibrillation which may be used in conjunction with the present invention.

FIG. 3 is a view of the heart and a plan view of an alternative implantable pacing, cardioversion and defibrillation head system which may be employed in conjunction with the present invention. This figure illustrates an epicardial electrode system of the sort that may be present in patients who previously have had implantable cardioverter/defibrillators implanted. The electrode system includes two enlarged epicardial electrodes 50, 52, and a third such electrode located on the backside of the heart, not visible in this view. These electrodes are coupled to the implantable cardioverter/defibrillator by means of insulated conductors 54, 56 and 58. The epicardial electrodes may correspond to those disclosed in U.S. Pat. No. 4,817,634, issued to Holleman et al. on Apr. 4, 1989, incorporated herein by reference in its entirety. Also included are two epicardial pacing/sensing electrodes 60 and 62, mounted adjacent the apex of the heart and coupled to the implantable cardioverter/defibrillator by means of insulated conductors 64 and 66. These epicardial leads may correspond to the leads disclosed in U.S. Pat. No. 3,737,579, issued to Bolduc on June 5, 1973, also incorporated herein by reference in its entirety.

An oxygen sensing lead 68 is also shown, with its location indicated by broken line. Its distal tip 70 is located in the apex of the right ventricle, in this embodiment, and the oxygen sensor thereon is also located within the right ventricle. The lead is provided with two mutually insulated conductors illustrated schematically at 72 and 74 and otherwise corresponds exactly to lead 18 illustrated in FIG. 2.

Figure 4:
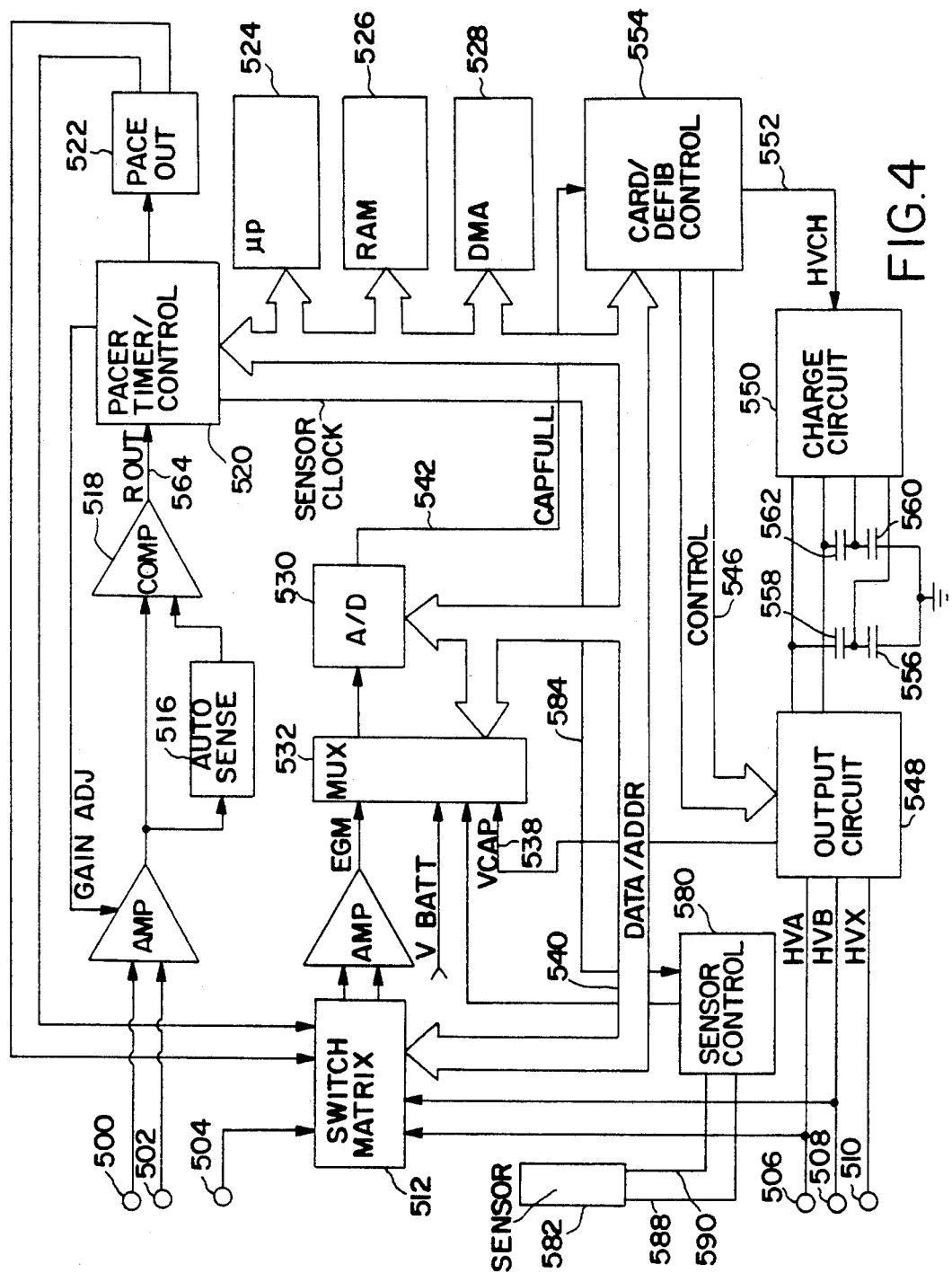
FIG. 4 is a schematic block diagram illustrating the structure of one embodiment of an implantable pacemaker/cardioverter/defibrillator in which the present invention may be embodied.

FIG. 4 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemaker/defibrillator/cardioverters presently being implanted for clinical evaluation in the United States. The invention is also believed practicable in conjunction with implantable pacemaker/cardioverters/defibrillators as disclosed in prior U.S. Pat. No. 4,548,209, issued to Wielders, et al on Oct. 22, 1985, U.S. Pat. No. 4,693,253, issued to Adams et al on Sept. 15, 1987, U.S. Pat. No. 4,830,006, issued to Haluska et al on May 6, 1989 and U.S. Pat. No. 4,949,730, issued to Pless et al on Aug. 21, 1990, all of which are incorporated herein by reference in their entireties.

The device is illustrated as being provided with six electrodes, 500, 502, 504, 506, 508 and 510. Electrodes 500 and 502 may be a pair of electrodes located in or on the ventricle, for example, corresponding to electrodes 10 and 12 in FIG. 2. Electrode 504 may correspond to a remote, indifferent electrode located on the housing of the implantable pacemaker/cardioverter/defibrillator.

Electrodes 506, 508 and 510 may correspond to the large surface area electrodes located on the ventricular and coronary sinus leads 6 and 8 illustrated in FIG. 2, in conjunction with a subcutaneous electrode or may correspond to the epicardial electrodes of FIG. 3.

Electrodes 500 and 502 are coupled to the R-wave detector circuit, comprising bandpass filter circuit 514, and automatic gain control circuit 516 for providing an adjustable sensing threshold as a function of the measured R-wave amplitude and a comparator 518. A signal is generated on R-out line 564 whenever the signal sensed between electrodes 500 and 502 exceeds the present sensing threshold defined by the automatic threshold adjustment circuit 516. As illustrated, the gain on the band pass amplifier 514 is also adjustable by means of a signal from the pacer timing and control circuitry 520 on GAIN ADJ line 566.

The operation of this R-wave detection circuitry may correspond to that disclosed in commonly assigned, copending U.S. patent application Ser. No. 07/612,760, by Keimel, et al., filed Nov. 15, 1990 for an Apparatus for Monitoring Electrical Physiologic Signals, incorporated herein by reference in its entirety. However, alternative R-wave detection circuitry such as that illustrated in U.S. Pat. No. 4,819,643, issued to Menken on Apr. 11, 1989, U.S. Pat. No. 4,880,004, issued to Baker et al on Nov. 14, 1989 and U.S. Pat. No. 4,240,442, issued to Andresen et al on Dec. 13, 1980, all incorporated herein by reference in their entireties, may also usefully be employed to practice the present invention.

For purposes of the present application, it should be understood that the threshold adjustment circuit 516 sets a threshold corresponding to a predetermined percentage of the amplitude of a sensed R-wave, which threshold decays to a minimum threshold level over a period of less than three seconds thereafter, similar to the automatic sensing threshold circuitry illustrated in the article "Reliable R-Wave Detection from Ambulatory Subjects", by Thakor et al, published in Biomedical Science Instrumentation, Vol. 4, pp 67–72, 1978, incorporated herein by reference in its entirety. However, in the context of the present invention, it is preferable that the threshold level not be adjusted in response to paced R-waves, but instead should continue to approach the minimum threshold level following paced R-waves to enhance sensing of low level spontaneous R-waves associated with tachyarrhythmias. The time constant of the threshold circuit is also preferably sufficiently short so that minimum sensing threshold may be reached within 1–3 seconds following adjustment of the sensing threshold equal to 70–80% of the amplitude of a detected spontaneous R-wave. The invention may also be practiced in conjunction with more traditional R-wave sensors of the type comprising a band pass amplifier and a comparator circuit to determine when the bandpassed signal exceeds a predetermined, fixed sensing threshold.

Switch matrix 512 is used to select which of the available electrodes make up a second electrode pair for use in sensing the electrical activity of the heart. The second electrode pair may comprise electrode 502 or 500 in conjunction with electrode 504, 506, 508 or 510, or may comprise other combinations of the illustrated electrodes. Selection of electrodes are controlled by the microprocessor 524 via data/address bus 540. Signals from the selected electrodes are passed through bandpass amplifier 534 and into multiplexer 532, where they may be converted to multibit digital signals by A/D converter 530, for storage in random access memory 526. Preferably, a portion of random access memory 526 is configured as a looping or buffer memory which can store at least the preceding several seconds of the ECG signal. The occurrence of an R-wave detect signal on line 564 is communicated to microprocessor 524 via data/address bus 540, and microprocessor 524 notes the time of its occurrence.

If the second electrode pair is used, microprocessor 524 waits 100 milliseconds following the occurrence of the R-wave detect signal, and thereafter transfers the most recent 200 milliseconds of digitized ECG stored in the looping or buffer memory portion of the random access memory circuit 526 to a second memory location, where the contents may be digitally analyzed under control of direct memory access circuit 528. Microprocessor 524 may analyze the digitized ECG signal stored in random access memory 526 to identify predetermined characteristics of the stored waveforms in conjunction with tachyarrhythmia detection and discrimination functions. For example, the point of maximum slope, the width or the area under each recorded R-wave may be determined.

Most of the remainder of the circuitry is dedicated to the provision of cardiac pacing, cardioversion and defibrillation therapies. The pacer timing/control circuitry 520 includes programmable digital counters which control the basic time intervals associated with VVI mode cardiac pacing, including the pacing escape intervals, the refractory periods during which sensed R-waves are ineffective to restart timing of the escape intervals and the pulse widths of the pacing pulses. The durations of these intervals are determined by microprocessor 526, and are communicated to the pacing circuitry 520 via address/data bus 540. Pacer timing/control circuitry 520 also determines the amplitude of the cardiac pacing pulses and the gain of bandpass amplifier, under control of microprocessor 524.

During VVI mode pacing, the escape interval counter within pacer timing/control circuitry 520 is reset upon sensing of an R-wave as indicated by a signal on line 564, and on timeout triggers generation of a pacing pulse by pacer output circuitry 522, which is coupled to electrodes 500 and 502. The escape interval counter is also reset on generation of a pacing pulse, and thereby controls the basic timing of all cardiac pacing functions, including anti-tachy pacing. The duration of the interval defined by the escape interval timer is determined by microprocessor 524, via data/address bus 540. The value of the count present in the escape interval counter when reset by sensed R-waves may be used to measure the duration of R—R intervals, to detect the presence of tachycardia and to determine whether the minimum rate criteria are met for activation of the discrimination function.

Microprocessor 524 operates as an interrupt driven device, and is awakened by interrupts from pacer timing/control circuitry 520 corresponding to the occurrence of sensed R-waves and corresponding to the generation of cardiac pacing pulses. These interrupts are provided via data/address bus 540. Any necessary mathematical calculations to be performed by microprocessor 524 and any updating of the values or intervals controlled by pacer timing/control circuitry 520 take place following such interrupts.

While not disclosed in detail herein, it is of course possible to employ the measurement of oxygen saturation to regulate the ventricular escape interval to provide rate responsive pacing. In such case, the microprocessor 224 could activate sensor 582 once in response to each sensed R-wave and each ventricular pacing pulse, except during delivery of antitachyarrhythmia therapies. The measurements so obtained could be used to calculate the VVIR escape interval as disclosed in the above cited Moore et al patent.

When interrupted in response to delivery of a ventricular pacing pulse or in response to sensing of a ventricular contraction, microprocessor 524 stores the duration of the measured R—R interval in random access memory 526. Preferably, a portion of memory 526 is configured as a recirculating buffer capable of storing the R—R intervals measured over the preceding 5 to 30 minutes. These stored R—R intervals may be used for tachycardia detection. Alternatively, the measured durations of the R—R intervals may be divided into rate classes and counts kept of the relative numbers of the preceding sequence of intervals which fall into the various rate classes, and these counts may be used for tachyarrhythmia detection and classification.

Detection of tachycardia and fibrillation, may correspond to any tachycardia and fibrillation detection algorithms known to the art. For example, presence of tachycardia may be confirmed by means of a measurement of average rate, sustained rate, rapid onset, rate stability, or a number of other factors known to the art. Detection algorithms for recognizing fibrillation and tachycardias are described in the above cited U.S. Pat. No. 4,726,380, issued to Vollmann, U.S. Pat. No. 4,880,005, issued to Pless et al and U.S. Pat. No. 4,830,006, issued to Haluska et al. An additional set of tachycardia and fibrillation recognition methodologies is disclosed in the article "Onset and Stability for Ventricular Tachyarrhythmia Detection in an Implantable Pacer-Cardioverter-Defibrillator" by Olson et al., published in *Computers in Cardiology*. Oct. 7-10, 1986, IEEE Computer Society Press, pages 167-170. However, one of the advantages of the present invention is that it is believed practicable in conjunction with virtually any prior art tachycardia detection algorithm.

In the event that a tachyarrhythmia is detected, and an antitachyarrhythmia pacing regimen is desired, appropriate timing intervals for controlling generation of antitachy pacing therapies are loaded from microprocessor 524 into the pacer timing and control circuitry 520, to control the operation of the escape interval counter therein and to define refractory periods during which detection of an R-wave by the R-wave detection circuitry is ineffective to restart the escape interval counter. Similarly, in the event that generation of a cardioversion or defibrillation pulses required, microprocessor 524 employs the escape interval counter to control timing of such cardioversion and defibrillation pulses, as well as associated refractory periods during which sensed R-waves are ineffective to reset the timing circuitry.

In response to the detection of either fibrillation or a tachycardia requiring a cardioversion pulse, microprocessor 524 activates cardioversion/defibrillation control circuitry 554, which initiates charging of the high voltage capacitors 556, 558, 560 and 562 via charging circuit 550, under control of high voltage charging line 552. The voltage on the high voltage capacitors is monitored via VCAP line 538, which is past through multiplexer 532, and, in response to reaching a predetermined value set by microprocessor 524, results in generation of a logic signal on CAP FULL line 542, terminating charging. Thereafter, the timing of the defibrillation or cardioversion pulse is controlled by pacer timing-/control circuitry 520.

One embodiment of an appropriate system for delivery and synchronization of cardioversion and defibrillation pulses, and controlling the timing functions related to them is disclosed in more detail in copending, commonly assigned U.S. patent application Ser. No. 07/612,761, by Keimel, for an Apparatus for Detecting and Treating a Tachyarrhythmia, filed Nov. 15, 1990 and incorporated herein by reference in its entirety. However, any known cardioversion or defibrillation pulse generation circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed. Similarly, known circuitry for controlling the timing and generation of antitachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In modern implantable cardioverter/defibrillators, the particular pacing, cardioversion and defibrillation therapies are programmed into the device by the physician, and a menu of therapies is typically provided. For example, on initial detection of tachycardia, an antitachy pacing therapy may be selected. On redetection of tachycardia, a more aggressive antitachy pacing therapy may be scheduled. If repeated attempts at antitachy pacing therapies, a higher level cardioversion pulse may be selected thereafter. Prior art patents illustrating such pre-set therapy menus of antitachyarrhythmia therapies include the above-cited U.S. Pat. No. 4,830,006, issued to Haluska, et al, U.S. Pat. No. 4,727,380, issued to Vollmann et al and U.S. Pat. No. 4,587,970, issued to Holley et al. The present invention is believed practicable in conjunction with any of the known antitachy pacing, cardioversion and defibrillation therapies, and it is believed most likely that the invention of the present application will be practiced in conjunction with a device in which the choice and order of delivered therapies is programmable by the physician, as in current implantable pacemaker/cardioverter/defibrillators.

In the event that fibrillation is diagnosed, the typical therapy will be delivery of a high amplitude defibrillation pulse, typically in excess of 20 joules. As in the case of currently available implantable pacemakers/cardioverter/defibrillators, and as discussed in the above-cited references, it is envisioned that the amplitude of the defibrillation pulse may be incremented in response to failure of an initial pulse or pulses to terminate fibrillation.

Selection of the particular electrode configuration for delivery of the cardioversion or defibrillation pulses is controlled via output circuit 548, under control of cardioversion/defibrillation control circuitry 554 via control bus 546. Output circuit 548 determines which of the high voltage electrodes 506, 508 and 510 will be employed in delivering the defibrillation or cardioversion pulse regimen, and may also be used to specify a multielectrode, simultaneous pulse regimen or a multielectrode sequential pulse regimen. Monophasic or biphasic pulses may be generated. One example of circuitry which may be used to perform this function is set forth in commonly assigned copending patent application Ser. No. 07/612,758, filed by Keimel, for an Apparatus for Delivering Single and Multiple Cardioversion and Defibrillation Pulses, filed Nov. 14, 1990, incorporated herein by reference in its entirety. However, output control circuitry as disclosed in U.S. Patent No. 4,953,551, issued to Mehra et al on Sept. 4, 1990 or U.S. Pat. No. 4,800,883, issued to Winstrom on Jan. 31, 1989 both incorporated herein by reference in their entireties, may also be used in the context of the present invention. Alternatively single monophasic pulse regimens employing only a single electrode pair according to any of the above cited references which disclose implantable cardioverters or defibrillators may also be used.

The oxygen sensing function of the present invention is performed by oxygen sensor 582, under control of sensor control circuitry 580. Sensor 582 and sensor control/decode circuitry 580 preferably correspond to the sensor and control circuitry disclosed in the above cited U.S. Pat. No. 4,750,495, issued to Moore et al. Sensor 582 corresponds to sensor 20, illustrated in FIG. 2 and is coupled to sensor control/decode circuitry 580 via two mutually insulated conductors 588 and 590.

As discussed in the above-cited Moore et al. patent, sensor control circuitry 580 provides a power signal to the sensor 582 via conductors 588 and 590. An oscillator within sensor 582 sequentially activates the red and infrared diodes therein, with the relative activation times reflecting the percentage of oxygen saturation of the hemoglobin within red blood cells. Because the red and infrared diodes draw differing levels of current, the current drawn by the sensor is modulated according the relative activation times of the red and infrared diodes, which modulation is decoded by sensor control/decode circuitry 580, which produces a voltage signal on line 586 indicative of measured oxygen saturation. This voltage signal is provided to the multiplexor 532 where it may be selected and provided to the direct converter memory access circuitry 528 by the microprocessor 524 via A to D converter 530. The sensor function may be disabled by programming of the device and, as discussed below, may be disabled in between measurement cycles associated with tachycardia detection or measurement of reference values. During such times as the sensor function is disabled, multiplexer 532 may be used to provide signals from amplifier 534 to A to D converter 530 for storage in memory 526.

Sensor control circuitry 580 is activated by a sensor clock signal on line 584 from pacer timer/control circuitry 520, with the sensor clock signal being a divided down clock signal taken from the to pacer timer/control circuitry which controls the escape interval timer, discussed above. In this fashion, activation of the oxygen sensor may be coordinated with the sensing of R-waves by pacemaker timing and control circuitry 520.

Activation of the sensor 582 is under control of microprocessor 524, and (other than for rate responsive pacing as discussed above) is only activated in cardiac cycles following interrupts indicative of R-waves sensed outside the refractory period defined by pacer timing and control circuitry 520. The sensor is not activated during cardiac cycles following delivery of pacing pulses, and the sensor function is disabled during delivery of all antitachyarrhythmia therapies, including antitachycardia pacing, cardioversion pulses and defibrillation pulses. Activation of the sensor function to allow discrimination of stable and unstable tachycardias is dependant on the patient's heart rhythm meeting a predetermined minimum criterion, hereafter referred to as the high rate criterion. The high rate criterion is preferably related to the tachycardia detection criteria, but is less stringent. The high rate criterion is defined such that it will always be met a sufficient number of cardiac cycles prior to the tachycardia detection criterion to allow sufficient measurement of the average oxygen saturation level and the oxygen saturation pulse amplitude. For example, if tachycardia is detected in response to a series of 20 short R—R interval, the high rate criterion could be satisfied by a series of 10 short R—R intervals, allowing 10 R—R intervals for measurement of oxygen saturation prior to tachycardia detection. Similarly, if a high heart rate persisting for 10 seconds is required to detect tachycardia, the high rate criterion may be satisfied by 5 seconds of high heart rate. It is believed preferable that the high rate criterion provide at least one second or four R—R intervals for oxygen saturation measurement prior to tachycardia detection.

Preferably, the oxygen saturation sensor 582 is activated with sufficient regularity during a cardiac cycle to allow for detection of the pulsatile characteristic of the oxygen saturation, as illustrated in FIG. 1. It is suggested that for this purpose, a sampling rate or a sensor clock rate of 200 hertz should be more than adequate. Alternatively, the activation frequency for the sensor may vary as a function of the sensed heart rate. For example, if the microprocessor 524 determines that the average heart rate in the period preceding the time at which the high rate criterion was met was 240 beats per minute (4 Hz), the microprocessor may instruct the pacer timing and control circuitry to provide a sensor activation signal at a frequency of 40 Hz on sensor clock line 584.

Under control of direct memory access circuitry 528, the measured values for oxygen saturation are stored in random access memory 526 for later analysis. Preferably, a portion of random access memory 526 is configured as a looping memory capable of storing the oxygen saturation values measured over at least the preceding 30 seconds to 2 minutes, if necessary. These measured oxygen saturation values are employed to distinguish between unstable tachycardias which require delivery of a defibrillation pulse and stable tachycardias which may be treated by means of lower level cardioversion pulses or antitachy pacing therapies. The operation of the oxygen sensor in performing this function is discussed in more detail in conjunction with the description of FIGS. 5,6 and 7, below.

While not disclosed in detail herein, it is believed that the present invention will most probably be practiced in a programmable device, with the values controlling tachyarrhythmia detection VVI pacing and the discriminator function will be entered into the device by means of a telemetry and programming system. Many of the programming and telemetry systems employed in the above cited patents are believed to be workable in the context of the present invention, as are the programming and telemetry systems employed by commercially marketed pacemakers and defibrillators. Moreover, it is anticipated that practical implementations of devices incorporating the invention will include the ability to store information related to the measurements of AVO2, AVPO2, REFO2 and REFPO2, discussed above. Storage of these measurements may take the form of histograms, as presently practiced in commercially marketed pacemakers employing physiologic sensors. Stored oxygen saturation measurements may also be associated with information stored in relation to detection of tachyarrhythmias and delivery of antitachyarrhythmia therapies to enable the physician to determine whether the discriminator is functioning properly.

Figure 5:
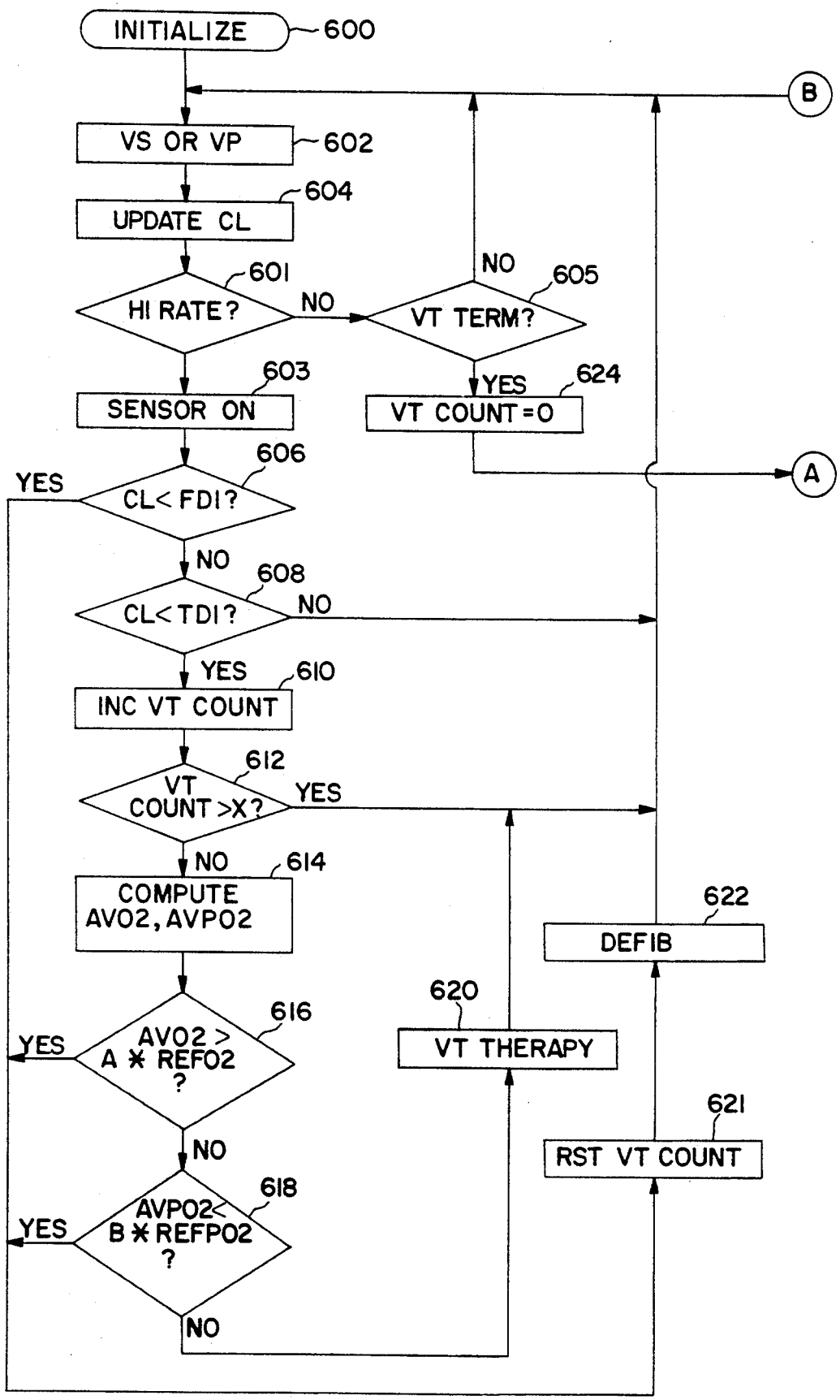
Figure 6:
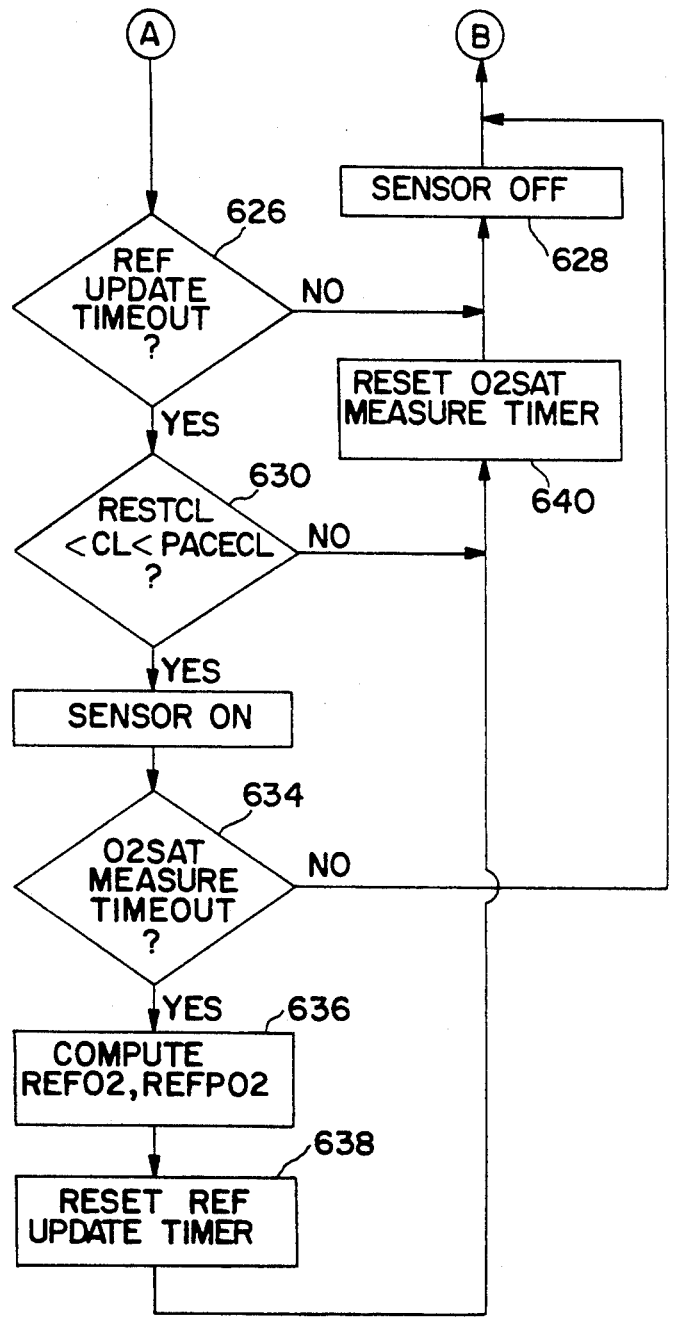

FIGS. 5, 6 and 7 are flow charts representing the operation of the device illustrated in FIG. 4, in conjunction with the discrimination function. FIGS. 5, 6 and 7 are intended to functionally represent that portion of the software employed by microprocessor 524 (FIG. 4) which implements the discrimination function.

Programmed parameters controlling the operation of the discrimination function include physician selected values for "A" and "B" which are percentage values chosen to measure the relationship between the currently measured oxygen saturation level and previously measured reference oxygen saturation values. "A" represents the minimum permissible presently measured average oxygen saturation level (AVO2) as compared to a previously measured average oxygen saturation level (REFO2), if unstable VT is to be identified. For example, "A" may be 70-95%, with the requirement that AVO2 be greater than A*REFO2 in order to detect unstable ventricular tachycardia requiring delivery of a defibrillation pulse.

The value of "B" represents the maximum allowable presently measured average oxygen saturation pulse amplitude (AVPO2) as compared to a previously measured reference value (REFPO2), if unstable VT is to be detected. For example, the value of "B" may be 20% to 50%, and AVPO2 being less than B*REFPO2 may serve as the precondition for detection of an unstable tachyarrhythmia and delivery of a defibrillation pulse.

Control parameters which affect the discrimination function also include the rest cycle length (RESTCL) and the pacing cycle length (PACECL). The pacing cycle length simply corresponds to the VVI mode pacing rate. The rest cycle length reflects a heart rate above the base pacing rate, but substantially below a rate which would indicate either strenuous exercise or the presence of tachycardia. For example, the pacing cycle length may be 1,000 milliseconds and the rest cycle length may be 750 milliseconds.

Also input by the physician are the fibrillation detection criteria (FDI) and the tachycardia detection criteria (TDI). These detection criteria may correspond to any known prior art detection criteria for identification of fibrillation and tachycardia. The high rate criterion is preferably defined in response to the selected tachycardia detection criteria, as discussed above. The present invention is believed useful in conjunction with any set of prior art detection criteria. However, for purposes of the present illustrative example, it may be presumed that the fibrillation detection criteria requires the detection of a cardiac rhythm having a cycle length which is predominantly less than a predetermined minimum fibrillation cycle length which continues to display such short cycle lengths for a minimum number of beats or a minimum period of time. It may also be presumed that the tachycardia detection criteria requires the detection of a cardiac rhythm having a cycle length which is predominantly less than a predetermined minimum tachycardia cycle length which continues to display such short cycle lengths for a minimum number of beats or a minimum period of time. Other detection criteria such as onset, rate stability, sustained high rate, and so forth may also be employed. However, these detection criteria are not reflected in the illustrative embodiments set forth in FIGS. 5, 6 and 7. Entry of the criteria discussed above is reflected at 600 as the initialization step.

On sensing of a ventricular depolarization or R-wave (VS) or delivery of a ventricular pacing pulse (VP) at 602, the microprocessor 524 is interrupted. The measured value (CL) of the R—R interval preceding the ventricular depolarization or ventricular pacing pulse is stored at 604. The preceding series of stored R—R intervals is examined at 601 to determine whether the high rate criterion is met, as discussed above. If the high rate criterion is met at 601, the sensor function is enabled at 603, and the microprocessor will thereafter activate the sensor following non-refractory sensed R-waves, as discussed above, until the sensor function is turned off.

If the high rate criterion is not met, the microprocessor examines the preceding series of stored R—R intervals at 605 to determine whether the patient is in sinus rhythm. This step may correspond to the tachycardia termination criteria as implemented in the prior art cardioverter/defibrillators discussed above, and may require, for example the detection of a series of long R—R intervals extending for a predetermined number of R—R intervals or for a predetermined time. If sinus rhythm or tachycardia termination is detected at 605, the VT count is set to 0 and the microprocessor checks to see whether new reference values are needed (FIG. 6). Otherwise, the microprocessor performs any other housekeeping and updating function that may be required, initiates the next VVI escape interval and awaits the next sensed R-wave or ventricular pacing pulse at 602.

If the high rate criterion was met at 601, the preceding sequence of stored cycle lengths is compared at 606 to the defined defibrillation detection criteria. In the event that the stored measured cycle lengths meet the fibrillation detection criteria, VTCOUNT is reset at 621 and a defibrillation pulse is delivered at 622. If the fibrillation criteria are not met at 606, the stored cycle lengths (R—R intervals) are reviewed at 608 to determine whether the tachycardia detection criteria are met. If the tachycardia detection criteria are met, VTCOUNT is incremented at 610. This count reflects the number of sequentially delivered antitachy pacing and/or cardioversion therapies.

The microprocessor checks to see whether the therapy count is in excess of a predetermined number "X" at 612. X will typically be four or more, depending on the number and variety of antitachyarrhythmia therapies available. If the therapy count is in excess of X at 612, the device assumes that the tachyarrhythmia is a sinus tachyarrhythmia or is otherwise untreatable, and no therapy is delivered.

In the event that VTCOUNT is less than or equal to X, the microprocessor 524 computes the present average values for oxygen saturation (AVO2) and for oxygen saturation pulse amplitude (AVPO2) from the measured values of oxygen saturation stored following the activation of the sensor function. As discussed above, the high rate and tachycardia detection criteria are so defined that oxygen saturation measurements for at least one second or four cardiac cycles are present in the random access memory 526 at this point. It may also in some cases be desirable to only consider the immediately preceding measurements of oxygen saturation for averaging purposes, if a significant time has passed between sensor activation and tachycardia detection. For example, a maximum of 10 seconds or 40 preceding cardiac cycles might be imposed.

After calculation of the values of AVO2 and AVPO2 at 614, these values are stored in random access memory 526, and are thereafter compared to the reference average oxygen saturation and oxygen saturation pulse amplitudes REFO2 and REFPO2, respectively, discussed above. AVO2 is compared to A*REFO2 at 616 to determine whether a significant change in measured oxygen saturation has occurred. In the event that no significant change in measured saturation as compared the reference level has occurred, an unstable ventricular tachycardia is diagnosed, and a defibrillation pulse is delivered at 622. In the event that AVO2 reflects a substantial decrease from REFO2, the value of AVPO2 is compared to B*REFPO2 at 618 to determine whether the oxygen saturation pulse amplitude has decreased. If a substantial decrease in oxygen saturation pulse amplitude is detected, the tachycardia is diagnosed as an unstable tachycardia and is treated by means of a defibrillation pulse at 622. If no substantial decrease in measured oxygen saturation pulse amplitude is detected at 618, the tachycardia is diagnosed as a stable VT, and is treated by means of antitachy pacing or cardioversion therapies at 620. As discussed above, the sensor function is disabled during the delivery of antitachyarrhythmia therapies.

FIG. 6 illustrates the procedure by which the values of REFO2 and REFPO2 are obtained. In response to the determination at 605 (FIG. 5) that the patient is in sinus rhythm or that tachycardia has terminated, the microprocessor checks at 626 to see whether a predetermined number of hours (e.g. 24 hours) has elapsed from the previous calculation of the reference values, using the real time clock of the microprocessor. If this reference update period has not timed out, the sensor function is turned off at 628 if previously enabled and the microprocessor returns the device to VVI pacing and awaits the next sensed R-wave or pacing pulse at 602 (FIG. 5).

In the event that the reference update period has timed out at 626, the microprocessor checks at 630 to determine whether the stored R—R intervals reflecting the previous 5–10 minutes indicate that the patient has maintained a heart rate greater than the VVI pacing rate, but below a rate indicative of either high activity or tachycardia, for example a rate between 60 and 80 beats per minute (1000–750 ms cycle length). If the patient is found to be in a resting state according to these criteria, the sensor function is activated at 632.

The microprocessor then checks to determine whether the oxygen saturation reference measurement interval has expired at 634. The reference measurement interval may be 5 seconds to 2 minutes, and represents the time period over which the reference values are averaged. If this interval is not expired, the microprocessor returns the device to VVI pacing, and measurements of oxygen saturation are continued until either the patient's rate goes outside of the rate range defined at 632 or the measurement interval expires at 634. On expiration of the measurement interval at 634, the measured values of oxygen saturation are used to compute new values for REFO2 and REFPO2 at 636. The reference update period is reset at 638, the measurement interval is reset at 640, the sensor function is disabled at 628 and the device returns to VVI pacing until the next sensed R-wave or pacing pulse at 602 (FIG. 5).

If the patient's heart rate falls outside the band defined at 630, any measurement cycle in progress is aborted, the measurement interval is reset at 640 and the sensor function is disabled until the rate returns to the specified range. In the event that the patient undergoes a tachycardia during a measurement cycle, the reference measurement function will of course be interrupted and will not effectively be resumed until detected termination of the tachycardia followed by a period of heart rhythm within the range specified at 630.

FIG. 7 represents an alternative embodiment of the present invention. Functional blocks in FIG. 7 which correspond to functional blocks in FIG. 5 are correspondingly labeled. For example, block 602 in FIG. 5 corresponds to block 702 in FIG. 7. Thus, all functional blocks from FIG. 5 are duplicated in FIG. 7. However, FIG. 7 reflects a rearrangement of the discrimination function.

At 715, in the event that the VT count indicates that this is the first antitachycardia therapy, stable ventricular tachycardia is diagnosed in the presence of either a decrease in average oxygen saturation level at 716b or in response to maintenance of the oxygen saturation pulse amplitude at 718b. Both a substantial decrease in the present oxygen saturation pulse amplitude at 716b and a stable average oxygen saturation level at 718b are required for diagnosis of unstable tachyarrhythmia and delivery of a defibrillation pulse at 722.

However, if the VT count at 715 indicates that this is the second or higher number tachycardia therapy, either the maintenance of the average oxygen saturation level at 716a or a decrease in oxygen saturation pulse amplitude at 718a will suffice to diagnose unstable tachycardia and trigger delivery of a defibrillation pulse at 722.

The operation of the device illustrated in FIG. 7 thus provides for a shift in criteria for the stable/unstable ventricular tachycardia discrimination. For the initial therapy the discriminator is less likely to diagnose unstable ventricular tachycardia than for the second and subsequent therapies. This feature allows the device to respond to a stable tachycardia that has thereafter become unstable, while imposing a more stringent criterion for diagnosis of an unstable ventricular tachyarrhythmia than in the system illustrated in FIG. 5. In the case of transition from stable to unstable tachyarrhythmia, loss of oxygen saturation pulse amplitude on the transition to unstable ventricular tachycardia will be the only diagnostic criteria met, as the average oxygen saturation level will previously have decreased in response to the stable ventricular tachycardia. The operations diagrammed in FIG. 7 interrelate with the reference measurement operations diagrammed in FIG. 6 in precisely the same manner as in the case of FIG. 5.

The scope of the invention should not be construed as limited by the functional schematic of FIG. 4, which, like FIGS. 5, 6 and 7 should be considered illustrative, rather than limiting with regard to the scope of the claims that follow. Furthermore, it should be recognized that although the disclosed embodiment deals with fibrillation and tachycardia in the lower chambers or ventricles of the heart, the invention might also be usefully practiced in the context of the upper chambers or atria of the heart, which are also prone to tachycardia and fibrillation in some patients.

In addition, while the therapies discussed in conjunction with the disclosed embodiment generally relate to delivery of electrical pulses, it should be understood that the invention may be usefully practiced in conjunction with any device adapted to deliver differing therapies for tachycardia and fibrillation, including drug therapies, non-pulsatile electrical therapies, and any other such therapies as may be implemented in such devices as their development progresses, whether applied directly to the heart or systemically. Similarly, it should be understood that the discriminator of the present invention, while particularly adapted for use in or in conjunction with an implantable cardioverter/defibrillator may also in some cases be usefully practiced in conjunction with a non-implantable device or even in a device adapted primarily for diagnostic purposes.

The claims below include the word "cardioverter", which in the context of the claims is used in its broadest sense, meaning any device which delivers a therapy intended to terminate a tachyarrhythmia, whether by cardiac pacing, intermediate level cardioversion shocks, high amplitude defibrillation pulses or other methods.

In conjunction with above application, we claim:

1. A cardioverter, comprising:
   therapy means for delivering a first therapy for termination of stable tachyarrhythmias and a second therapy for termination of unstable tachyarrhythmias to a patient's heart;
   detection means for sensing the rhythm of said patients heart and for detecting the presence of a tachyarrhythmia;
   an oxygen saturation sensor means for measuring the current level of oxygen saturation of the hemoglobin of the venous return blood in said patient's heart;
   reference means responsive to said sensor for storing a measured level of oxygen saturation as a reference level of oxygen saturation;
   discriminator means responsive to said detection means, said sensor means and said reference means for detecting the presence of an unstable tachyarrhythmia in response to the detection of a tachyarrhythmia by said detecting means and a measured current level of oxygen saturation which varies less than a predetermined amount from said reference level of oxygen saturation and for triggering said therapy means to deliver said second therapy in response to the detection of said unstable tachyarrhythmia.

2. A cardioverter according to claim 1 wherein said means for measuring the current level of oxygen saturation comprises means for taking a plurality of individual oxygen saturation measurements and for defining said current level of oxygen saturation as an average of a plurality of said individual oxygen saturation measurements and said reference means comprises means for defining and storing an average of a plurality of said individual oxygen saturation measurements.

3. A cardioverter according to claim 2 wherein said reference means comprises means for detecting that said patient is in a resting state and wherein said reference means comprises means for deriving and storing said reference level of oxygen saturation as an average of said individual oxygen saturation measurements taken while said patient is in said detected resting state.

4. A cardioverter according to claim 3 wherein said means for detecting that said patient is in a resting state comprises means responsive to said for sensing the rhythm of said patient's heart and for identifying the sensed rhythm of said patient's heart as indicative of a resting state.

5. A cardioverter according to claim 4 wherein said means for detecting that said patient is in a resting state comprises means responsive to the heart rhythm sensed by said means for sensing the rhythm of said patient's heart and for identifying the sensed rhythm of said patient's heart as indicative of a resting state.

6. A cardioverter, comprising:
therapy means for delivering a first therapy for termination of stable tachyarrhythmias and a second therapy for termination of unstable tachyarrhythmias to a patient's heart;
detection means for sensing the rhythm of said patients heart and for detecting the presence of a tachyarrhythmia;
an oxygen saturation sensor means for measuring the oxygen saturation level of the hemoglobin of the venous return blood in said patient's heart and for deriving a measurement of the amplitude of the current pulsatile character of the measured oxygen saturation level;
reference means responsive to said sensor for storing a measurement of the amplitude of the pulsatile character of the level of oxygen saturation as a reference oxygen saturation pulse amplitude;
discriminator means responsive to said detection means, said sensor means and said reference means, for detecting the presence of an unstable tachyarrhythmia in response to the detection of a tachyarrhythmia by said detecting means and a measured current amplitude of the pulsatile character of the level of oxygen saturation which is less than said reference oxygen saturation pulse amplitude by a predetermined amount and for triggering said therapy means to deliver said second therapy in response to the detection of said unstable tachyarrhythmia.

7. A cardioverter according to claim 6 wherein said means for deriving a measurement of the amplitude of the current pulsatile character of the measured oxygen saturation level comprises means for taking a plurality of individual oxygen saturation pulse amplitude measurements and for deriving said amplitude of said current pulsatile character of said oxygen saturation level as an average of a plurality of said individual oxygen saturation pulse amplitude measurements and said reference means comprises means for defining said reference oxygen saturation pulse amplitude means comprises means for deriving and storing an average taken over a plurality of said individual oxygen saturation pulse amplitude measurements.

8. A cardioverter according to claim 7 wherein said reference means comprises means for detecting that said patient is in a resting state and wherein said reference means comprises means for deriving and storing an average of said oxygen saturation pulse amplitude measurements taken while said patient is in said detected resting state.

9. A cardioverter, comprising:
therapy means for delivering a first therapy for termination of stable tachyarrhythmias and a second therapy for termination of unstable tachyarrhythmias to a patient's heart;
detection means for sensing the rhythm of said patients heart and for detecting the presence of a tachyarrhythmia;
an oxygen saturation sensor means for measuring the current level of oxygen saturation of the hemoglobin of the venous return blood in said patient's heart and for deriving a measurement of the amplitude of the current pulsatile character of the measured oxygen saturation level;
reference means responsive to said sensor for storing a measured level of oxygen saturation as a reference level of oxygen saturation and for storing a measurement of the amplitude of the pulsatile character of the level of oxygen saturation as a reference oxygen saturation pulse amplitude;
discriminator means responsive to said detection means, said sensor means and said reference means, for detecting the presence of an unstable tachyarrhythmia in response to the detection of a tachyarrhythmia by said detecting means, to the difference between said measured current level of oxygen saturation and said reference level of oxygen saturation and to the difference between said measured current amplitude of the pulsatile character of the level of oxygen saturation and said reference oxygen saturation pulse amplitude and for triggering said therapy means to deliver said second therapy in response to the detection of said unstable tachyarrhythmia.

10. A cardioverter according to claim 9 wherein said discriminator means comprises means for detecting the presence of said unstable tachyarrhythmia in response to a measured current amplitude of the pulsatile character of the level of oxygen saturation which is less than said reference oxygen saturation pulse amplitude by a predetermined amount in conjunction with a measured current level of oxygen saturation which varies less than a predetermined amount from said reference level of oxygen saturation.

11. A cardioverter according to claim 9 wherein said discriminator means comprises means for detecting the presence of said unstable tachyarrhythmia in response to a measured current amplitude of the pulsatile character of the level of oxygen saturation which is less than said reference oxygen saturation pulse amplitude by a predetermined amount or in response to a measured current level of oxygen saturation which varies less than a predetermined amount from said reference level of oxygen saturation.

12. A cardioverter according to claim 1 or claim 6 or claim 9 wherein said discriminator means further comprises means for triggering said therapy means to deliver said second therapy in response to the detection of a tachyarrhythmia by said detector means in the absence of detection of an unstable tachyarrhythmia by said discriminator means.

13. A cardioverter according to claim 12 wherein said means for providing said first therapy comprises means for delivering a defibrillation pulse to said patient's heart.

14. A cardioverter according to claim 13 wherein said means for providing said second therapy comprises means for delivering of an electrical pulse of less amplitude than said defibrillation pulse to said patient's heart.

15. A cardioverter according to claim 14 wherein said means for providing said second therapy comprises means for delivering a cardioversion pulse.

16. A cardioverter according to claim 14 wherein said means for providing said second therapy comprises means for delivering a cardiac pacing pulse.

17. A cardioverter, comprising:

therapy means for delivering a therapy for termination of unstable tachyarrhythmias to a patient's heart;

detection means for sensing the rhythm of said patient's heart and for detecting the presence of a tachyarrhythmia;

an oxygen saturation sensor means for measuring the current level of oxygen saturation of the venous return blood in said patient's heart;

reference means responsive to said sensor for storing a measured level of oxygen saturation as a reference level of oxygen saturation;

discriminator means responsive to said detection means, said sensor means and said reference means, for detecting the presence of an unstable tachyarrhythmia in response to the detection of a tachyarrhythmia by said detecting means and a measured current level of oxygen saturation which varies less than a predetermined amount from said reference level of oxygen saturation and for triggering said therapy means to deliver said therapy in response to the detection of said unstable tachyarrhythmia.

18. A cardioverter, comprising:

therapy means for delivering a therapy for termination of unstable tachyarrhythmias to a patient's heart;

detection means for sensing the rhythm of said patients heart and for detecting the presence of a tachyarrhythmia;

an oxygen saturation sensor means for measuring the oxygen saturation level of the hemoglobin of the venous return blood in said patient's heart and for deriving a measurement of the amplitude of the current pulsatile character of the measured oxygen saturation level;

reference means responsive to said sensor for storing a measurement of the amplitude of the pulsatile character of the level of oxygen saturation as a reference oxygen saturation pulse amplitude;

discriminator means responsive to said detection means, said sensor means and said reference means, for detecting the presence of an unstable tachyarrhythmia in response to the detection of a tachyarrhythmia by said detecting means and a measured current amplitude of the pulsatile character of the level of oxygen saturation which is less than said reference oxygen saturation pulse amplitude by a predetermined amount and for triggering said therapy means to deliver said therapy in response to the detection of said unstable tachyarrhythmia.

19. A discriminator, comprising:

detection means for sensing the rhythm of said patients heart and for detecting the presence of a tachyarrhythmia;

an oxygen saturation sensor means for measuring the current level of oxygen saturation of the hemoglobin of the venous return blood in said patient's heart;

reference means responsive to said sensor for storing a measured level of oxygen saturation as a reference level of oxygen saturation;

discriminator means responsive to said detection means, said sensor means and said reference means, for detecting the presence of an unstable tachyarrhythmia in response to the detection of a tachyarrhythmia by said detecting means and a measured current level of oxygen saturation which varies less than a predetermined amount from said reference level of oxygen saturation.

20. A discriminator, comprising:

detection means for sensing the rhythm of said patients heart and for detecting the presence of a tachyarrhythmia;

an oxygen saturation sensor means for measuring the oxygen saturation level of the hemoglobin of the venous return blood in said patient's heart and for deriving a measurement of the amplitude of the current pulsatile character of the measured oxygen saturation level;

reference means responsive to said sensor for storing a measurement of the amplitude of the pulsatile character of the level of oxygen saturation as a reference oxygen saturation pulse amplitude;

discriminator means responsive to said detection means, said sensor means and said reference means, for detecting the presence of an unstable tachyarrhythmia in response to the detection of a tachyarrhythmia by said detecting means and a measured current amplitude of the pulsatile character of the level of oxygen saturation which is less than said reference oxygen saturation pulse amplitude by a predetermined amount.

* * * * *